(12) United States Patent
Ghosh et al.

(10) Patent No.: US 10,234,445 B2
(45) Date of Patent: Mar. 19, 2019

(54) AUTOMATED IMAGING OF CHROMOPHORE LABELED SAMPLES

(71) Applicant: CELLOMICS, INC., Pittsburgh, PA (US)

(72) Inventors: Richik Niloy Ghosh, Upper St. Clair, PA (US); Dirk John VandenBerg, III, Pittsburgh, PA (US); Keith Rao Heffley, Pittsburgh, PA (US); Monica Jo Tomaszewski, Pittsburgh, PA (US); Jeffrey Robert Haskins, Mars, PA (US)

(73) Assignee: CELLOMICS, INC., Pittsburgh, PA (US)

( * ) Notice: Subject to any disclaimer, the term of this patent is extended or adjusted under 35 U.S.C. 154(b) by 57 days.

(21) Appl. No.: 15/594,978

(22) Filed: May 15, 2017

(65) Prior Publication Data

US 2017/0248574 A1    Aug. 31, 2017

Related U.S. Application Data

(62) Division of application No. 14/709,239, filed on May 11, 2015, now Pat. No. 9,683,939.

(Continued)

(51) Int. Cl.
*G01N 33/487* (2006.01)
*G01N 21/64* (2006.01)
(Continued)

(52) U.S. Cl.
CPC ......... *G01N 33/487* (2013.01); *G01N 21/253* (2013.01); *G01N 21/31* (2013.01);
(Continued)

(58) Field of Classification Search
CPC .................................................. G01N 33/487
(Continued)

(56) References Cited

U.S. PATENT DOCUMENTS 7,443,508 B1    10/2008    Vrhel et al.
7,812,952 B2    10/2010    Delaage et al.
(Continued)

FOREIGN PATENT DOCUMENTS

CN    102224260    10/2011
CN    102782559    11/2012
(Continued)

OTHER PUBLICATIONS

Scimson, "Photometry and Radiometry for Engineers" Edition 1, Science Press, 1974, pp. 185-188.
(Continued)

*Primary Examiner* — Tarifur R Chowdhury
*Assistant Examiner* — Omar H Nixon
(74) *Attorney, Agent, or Firm* — Workman Nydegger

(57) ABSTRACT

A system and method that images biological samples and uses chromophores to analyze the imaged samples. The chromophore analysis can be done by itself or in conjunction with fluorophore analysis in High Content Imaging systems. To perform chromophore analysis the biological samples can be labeled with different chromophores and imaged using transmitted light that is at least partially absorbed by the chromophores. To also perform fluorophore analysis the samples can also be labeled with fluorophores that are excited by excitation light. The chromophore analysis and fluorophore analysis can be performed separately or concurrently using a High Content Imaging system. The system provides the expanded capability by illuminating the chromophore-labeled samples with transmitted light of different wavelengths and automatically detecting the images which represent the differential absorption of the colored lights by the sample.

20 Claims, 11 Drawing Sheets

Related U.S. Application Data

(60) Provisional application No. 61/992,008, filed on May 12, 2014.

(51) Int. Cl.
| | |
|---|---|
| *G02B 5/02* | (2006.01) |
| *G01N 21/25* | (2006.01) |
| *G01N 21/31* | (2006.01) |
| *G01N 35/00* | (2006.01) |
| *G02B 21/16* | (2006.01) |
| *G02B 21/36* | (2006.01) |
| *F21Y 105/14* | (2016.01) |
| *F21Y 105/10* | (2016.01) |

(52) U.S. Cl.
CPC ..... *G01N 21/6428* (2013.01); *G01N 21/6452* (2013.01); *G01N 21/6458* (2013.01); *G01N 21/6486* (2013.01); *G01N 35/00029* (2013.01); *G02B 5/0278* (2013.01); *G02B 5/0294* (2013.01); *G02B 21/16* (2013.01); *G02B 21/367* (2013.01); *F21Y 2105/10* (2016.08); *F21Y 2105/14* (2016.08); *G01N 21/255* (2013.01); *G01N 2021/6439* (2013.01); *G01N 2021/6491* (2013.01); *G01N 2035/00158* (2013.01); *G01N 2201/0627* (2013.01)

(58) Field of Classification Search
USPC ........................................................ 356/417
See application file for complete search history.

(56) References Cited

U.S. PATENT DOCUMENTS

| | | |
|---|---|---|
| 7,894,079 B1 | 2/2011 | Altendorf et al. |
| 2002/0177149 A1 | 11/2002 | Rimm et al. |
| 2003/0127609 A1 | 7/2003 | El-Hage et al. |
| 2003/0231494 A1 | 12/2003 | Shimokawa et al. |
| 2007/0153847 A1 | 7/2007 | Faircloth et al. |
| 2008/0297774 A1 | 12/2008 | Jiang |
| 2009/0137908 A1* | 5/2009 | Patwardhan ......... A61B 5/0059 600/476 |
| 2012/0105600 A1 | 5/2012 | Meyer et al. |
| 2013/0041267 A1* | 2/2013 | Ntziachristos ..... A61B 1/00009 600/476 |
| 2013/0243284 A1 | 9/2013 | Babayoff |
| 2014/0160745 A1 | 6/2014 | Mandelboum et al. |
| 2015/0278625 A1 | 10/2015 | Finkbeiner et al. |
| 2015/0317506 A1 | 11/2015 | Xie et al. |

FOREIGN PATENT DOCUMENTS

| | | |
|---|---|---|
| CN | 103620378 | 3/2014 |
| EP | 2166082 A1 | 3/2010 |
| WO | 2012051638 A1 | 4/2012 |

OTHER PUBLICATIONS

"International Search Report and Written Opinion in PCT Application No. PCT/US2015/030210", dated Nov. 5, 2015, 17 Pages.

Wu, et al: "HTS technologies in biopharmaceutical discovery", Drug Discovery Today, Elsevier, Rahway, NJ, US, vol. 11, No. 15-16, Aug. 1, 2006 (Aug. 1, 2006), pp. 718-724, XP027889189, ISSN: 1359-6446.

European Search Results under Rule 164(2)(b) EPC in Application No. 15725460 dated Nov. 30, 2018.

European Office Action issued in Application No. 15725460.8 dated Dec. 6, 2018.

* cited by examiner

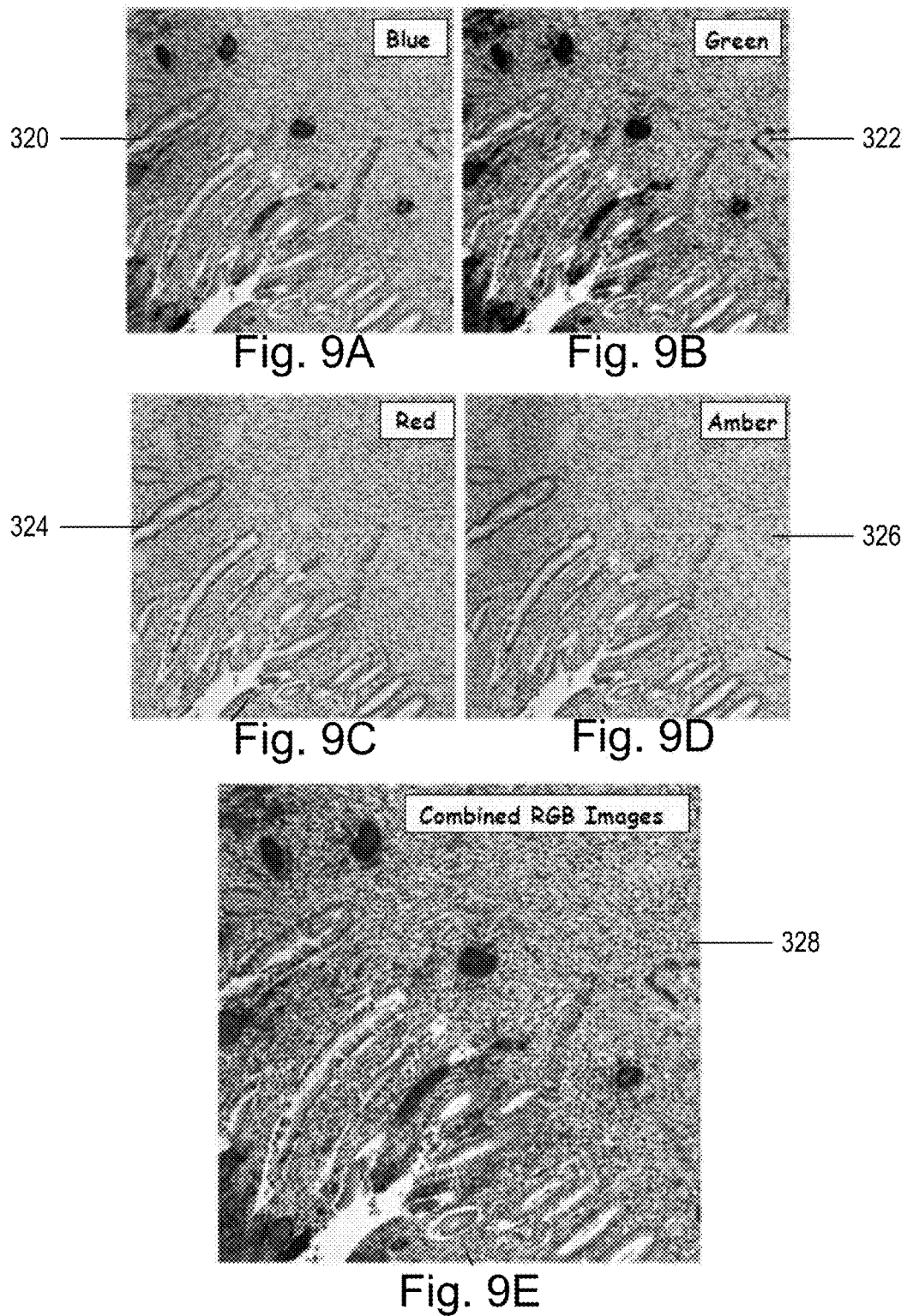

| Absorption Characteristics of Common Biological Stains ||
| Stain | Visible Absorption Spectral Profiles |
|---|---|
| Acid Fuchsin | 530-620 |
| Aniline Blue | 550-820 |
| Azure B | 580+ |
| Azure C | 580-640 |
| Basic Fuchsin | 500-570 |
| Brilliant Cresyl Blue | 550+ |
| Carmine | 500-570 |
| Congo Red | 400-560 |
| Crystal Violet | 550-610 |
| Darrow Red | 450-550 |
| Eosin Y | 490-530 |
| Erythrosin B | 510-540 |
| Ethyl Eosin | 530-550 |
| Fast Green | 560+ |
| Giemsa | 500+ |
| Light Green SF | 590+ |
| Luxol Fast Blue | 500-640 |
| Methyl Green | 500+ |
| Methylene Blue | 590+ |
| Nuetral Red | 480-570 |
| Nigrosin | 450+ |
| Nuclear Fast red | 460-550 |
| Orange G | 450-510 |
| Orcein | 500-620 |
| Phloxin B | 520+ |
| Prussian Blue | 560+ |
| Pyronin B | 350-480 |
| Saffron | 350-480 |
| Safranin O | 470-550 |
| Sudan IV | 470-580 |
| Sudan Red | 450-590 |
| Tartrazine | 400-460 |
| Toluidine Blue | 560+ |
| Trpan Blue | 500+ |
| Wright's | 500+ |
| Wavelength (nm)   400 | 500                600 |
| <Ultraviolet | Infrared> |

Fig. 11

AUTOMATED IMAGING OF CHROMOPHORE LABELED SAMPLES

CROSS-REFERENCE TO RELATED APPLICATIONS

This application is a divisional of U.S. patent application Ser. No. 14/709,239 filed on May 11, 2015, entitled "AUTOMATED IMAGING OF CHROMOPHORE LABELED SAMPLES," which issued as U.S. Pat. No. 9,683,939 on Jun. 20, 2017, which claims the benefit of and priority to U.S. Provisional Patent Application Ser. No. 61/992,008 filed on May 12, 2014, and entitled "AUTOMATED IMAGING OF CHROMOPHORE LABELED SAMPLES," both of which applications are incorporated herein by reference in their entirety.

BACKGROUND

1. The Field of the Invention

The present application relates to the use of automated imaging systems for high-content screening and analysis, collectively referred to as high-content imaging. More particularly, the present application relates to high-content imaging using a system having multiplexed imaging capabilities that include imaging of different chromophore labeled samples.

2. The Relevant Technology

A growing trend in microscopy over the last decade is the automated imaging of biological samples. Rather than the manual observation of samples, automated microscopy involves computer-controlled automatic selection and digital imaging of sample fields, enabling high throughput imaging of a large number of samples without end-user input.

Automated imaging is often known as HCI (High-Content Imaging) when applied to fluorescently labeled cells with automated quantitative analysis of the acquired images. In particular, HCI is a cell-based screening method that yields detailed information about the temporal-spatial dynamics of cell constituents and processes, and plays an important role in the use of cell-based screening for identification and validation of drug candidates. The information provided by HCI alleviates bottlenecks in the drug discovery process by providing deep biological information. The assays associated with this method use either fixed or live cells, depending on the biological information desired.

As an example HCI method of operation, the tissues or cells of interest are loaded onto a segment of a microscope slide or into an array of wells in a standard specimen plate (also known as a micro-titer or micro-well plate). The segment of the slide or specimen plate is then positioned on a stage within an imaging system so that the slide or specimen plate can move with the stage in both directions orthogonal to a configured light path of the system. Often the system includes a microscope for investigation of targeted cells. As a result, any of the individual wells or segment of the slide can be positioned in alignment with the microscope so as to be imaged through the microscope objective.

During a typical scan, the stage is moved by configured motors until one of the wells or segment of a slide is aligned with the objective and one or more of the cells within that well or segment of a slide are imaged through the objective. With respect to wells, the entire well can be imaged at the same time, or various fields within the well can be individually imaged.

When imaging is completed, the stage is then moved by the motors until another one of the wells or segment of a slide is aligned with the objective and, similar to the discussion above, one or more of the cells within the newly aligned micro-well or segment of a slide are imaged through the objective. This movement and imaging continues until all of, for example, the wells or defined segments of the slide have been imaged through the objective. Computerized analysis is then performed on the obtained images to determine information about the cells. This type of scanning can be performed many times a day for different HCI scans using the same machine.

HCI has mainly been applied on cells labeled with fluorescent probes, such as fluorescent ligands and immunofluorescent probes towards particular cellular targets, fluorescent environmental or cell state sensors, or fluorescent protein chimeras being endogenously expressed by the cell. For optimal signal-to-noise ratio detection, fluorescence typically requires using epifluorescence geometry of the imaging system, where the fluorescence signal retraces the same path as the illumination light, and the two are separated from each other by a wavelength discriminator such as a dichroic mirror, diffraction grating, or a solid-state discriminator such as an AOTF or LCTF. An added benefit to HCI is its multiplexed multispectral capability, where multiple fluorescent probes can be detected, each emitting fluorescence signal in a different color, as well as the ability to combine images acquired using white light brightfield imaging, which is an option available on most HCI platforms.

Brightfield microscopy uses a transmitted light geometry, wherein both the sample's illumination and the luminescent signals reaching the detector span the same wavelengths. However, the drawback to using brightfield microscopy when applied to biological samples is its poor contrast. Typically, the contrast can be enhanced by methods such as phase contrast and DIC (differential interference contrast) microscopy, where the sample illumination and the luminescent signal going to the detector still cover the same wavelengths.

An alternate approach to improve sample contrast and to distinguish specific cellular or tissue structures with transmitted light imaging is to stain the sample with different chromophores. Chromophores absorb light of specific wavelengths, and the differential absorption (i.e., subtractive mixing) and transmittance of transmitted light enhances the contrast of the sample. Additionally, depending on the different affinities various chromophores have for different areas of structures in cells and tissues, by the differential absorption of light by these chromophores these different cellular or tissue regions can be detected. The use of chromophores to differentially detect different cellular or tissue regions with high contrast, such as with H&E (hematoxylin and eosin) stains, is a routine and traditional use of microscopy in both life sciences research, as well as clinical diagnostic applications.

It is to be also noted that automated tissue scanners for digital pathology have the ability to image both fluorescence and chromophore absorbance but such methods are limited by either using multiple detectors to capture the primary colors or a color camera to capture the differential color absorptions by the chromophores. In addition, adding a color camera or multiple monochrome cameras can be expensive. Moreover, analysis of images acquired on a color camera, requires image processing algorithms that first unmix the different colors which is accomplished with the aid of reference images.

It is thus desirable to provide other cost-effective and automated systems and methodologies to improve sample contrast and to distinguish specific cellular or tissue structure that is complimentary to imaging of only fluorescently labeled cell types of automated imaging systems.

Accordingly, embodiments herein provide a system and method of High Content Imaging (HCI) on cell and/or tissue samples that are labeled with fluorescence probes and/or also labeled with chromophores. Since HCI is a multiplexed method where multiple different fluorescence colors, as well as white light brightfield imaging can be combined, the embodiments herein extend the capability of existing systems by including the ability to do multiplexed imaging with different chromophores using only a single detector.

BRIEF SUMMARY

Various embodiments disclosed herein are related to a High-Content Imaging (HCI) System that provides for HCI on cell and/or tissue samples labeled with fluorescence probes that can also be labeled with chromophores. Furthermore, the ability of HCI to multiplex different imaging modes means that any combination of three modes of operation, as detailed herein, can be used whereas previously only brightfield white light images could be combined with fluorescence. In particular, whereas previously only brightfield white light images could be combined with fluorescence, embodiments disclosed herein enhance HCI's capability to also be able to detect different differential color absorption by chromophores.

A first aspect provides for an automated method for analyzing cells that includes: providing an array of locations which contain a plurality of cells having one or more fluorescent reporter molecules and/or one or more chromophore stained molecules, wherein the plurality of cells in each of the locations are contained as a subset plurality of cells to provide for a plurality of fields; providing a light source configured to selectively direct one or more wavelengths of radiation to the plurality of fields in any of the array of locations; scanning each of the plurality of fields within one or more desired locations; providing multiple images for each field with a single monochrome camera, wherein each of the multiple images comprises induced fluorescent signals and/or induced chromophore absorption signals on or within the cells, wherein each image comprises at least one optical modality selected from: one or more excitation wavelengths of radiation, a selected filtered wavelength of radiation, and a desired imaging exposure period; comparing while imaging, each of the multiple images so as to convert the induced fluorescent signals and/or chromophore absorption signals from each of the multiple images into digital data; utilizing the digital data to automatically make measurements of intensity and/or distribution of the fluorescent signals from the fluorescent reporter molecules on or within cells and/or automatically make measurements of intensity and/or distribution of the chromophore induced absorption signals on or within the cells; and ability to combine and display images from various channels captured on the monochrome camera so they display on the computer screen as a high-contrast color image.

This increased capability enables applications previously not possible by HCI platforms, such as, but not limited to:
Automated imaging of chromophore stained tissues, & quantitative separation and analysis of color distributions;

Immunofluorescence on chromophore stained tissue—enables detecting specific molecular targets in tissue—all done in an automated manner for one or more samples; and Expanded optical modalities of up to 7λ, with λ, being a particular excitation light (such as, e.g., light emitting diode (LED) or filtered white light), a particular imaged light (usually filtered from what is received from the micro-well), and/or a particular exposure period, etc.

BRIEF DESCRIPTION OF THE DRAWINGS

Various embodiments will now be discussed with reference to the appended drawings. It should be appreciated that these drawings depict only typical embodiments and are therefore not to be considered limiting of the scope of the application. It should also be appreciated that the drawings are not necessarily drawn to scale and that some of the elements may be drawn merely for clarity sake.

In the drawings, like numerals designate like elements. Furthermore, multiple instances of an element may each include separate letters appended to the element number. For example two instances of a particular element "20" may be labeled as "20*a*" and "20*b*". In that case, the element label may be used without an appended letter (e.g., "20") to generally refer to every instance of the element; while the element label will include an appended letter (e.g., "20*a*") when referring to a specific instance of the element.

FIGS. 9A-9E show H&E stained tissue differential absorption images captured with a 10× objective using four different wavelengths.

FIG. 11 shows the absorption bands of common chromophores used for biological staining.

DETAILED DESCRIPTION

Figure 1:
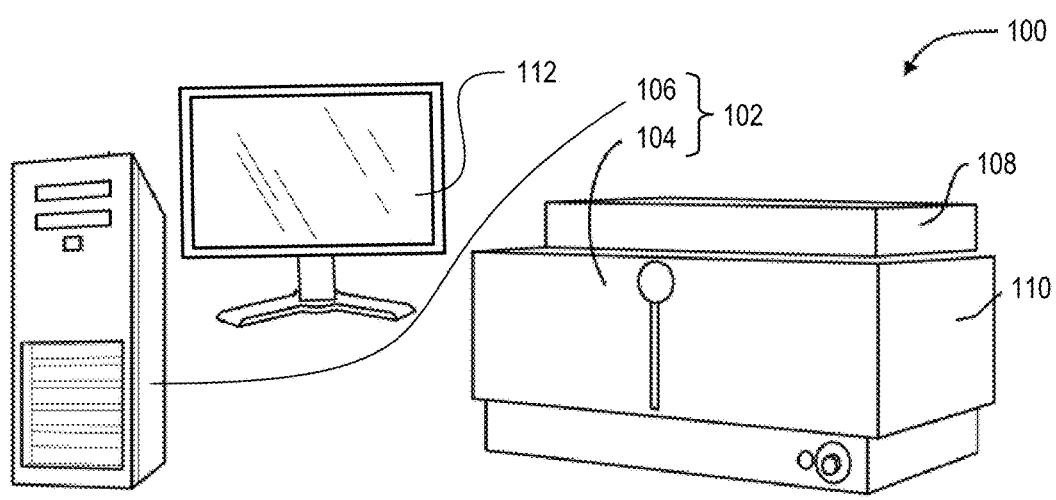
FIG. 1 illustrates an example embodiment of a system incorporating features disclosed or envisioned herein.

As used in the specification, a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Furthermore, as used in the specification and appended claims, directional terms, such as "top," "bottom," "left," "right," "up," "down," "upper," "lower," "proximal," "distal" and the like are used herein solely to indicate relative directions and are not otherwise intended to limit the scope of the specification or claims.

As briefly discussed in the background section, the emphasis with respect to HCI has typically been directed to optimizing the technology to detect fluorescence signals because imaging of chromophore stained biological samples has not previously, for disadvantageous reasons, been a methodology incorporated into HCI. However, while HCI of fluorescence cells and/or tissue is an often utilized method, the novel capability, as disclosed herein, of adding HCI of chromophore stained samples in an automated fashion is desirable as an added feature into HCI. For example, HCI of chromophores provides greater contrast of structures when illuminated with brightfield white light than if a sample is unlabeled and can thus provide additional important cell and/or tissue information to be added to HCI capabilities.

High content imaging (HCI) systems presented herein are thus directed to systems that can expand the capabilities of conventional HCI systems. Embodiments of HCI systems disclosed herein are not only able to image biological samples labeled with fluorophores and/or image samples using white light brightfield illumination, they can also image biological samples labeled with one or more chromophores in an automated multiplexed manner. This can be achieved by illuminating the chromophore-labeled samples with transmitted light of specific wavelengths and/or illuminating in an epifluorescent mode the fluorophores in the samples using different wavelengths and automatically detecting the images which represent the fluorescent information or differential absorption of the colored lights by the sample.

With respect to the transmitted light illumination set-up, the configuration, as disclosed herein, is built in combination with an epifluorescence microscopy platform designed for automated fluorescence imaging (i.e. high content screening (HCS)). The transmitted light wavelengths are transmitted through the optics (e.g. dichroic mirrors, emission filters, etc.) of the epifluorescence set-up to be able to reach a single detector or image recorder, such as a single monochrome camera (CCD).

As a result, the overall design provides for not only fluorescence imaging over the visible spectrum (i.e. from near-UV to near-IR), but provides an added capability of detecting chromophores that also absorb light over the span of the visible spectrum. Additionally, the disclosed design and methodology offers a relatively inexpensive way to upgrade fluorescence microscopes to be able to also detect chromophores without the need to use color cameras or multiple detectors for different wavelengths.

Embodiments disclosed or envisioned herein may comprise or utilize a special purpose or general-purpose computer including computer hardware, such as, for example, one or more processors, as discussed in greater detail below. Embodiments may also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments can comprise at least two distinctly different kinds of computer-readable media: computer storage media and transmission media.

Computer storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired and wireless) to a computer, the computer properly views the connection as a transmission medium. Transmission media can include a network and/or data links which can be used to carry data or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., an "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that embodiments may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, tablets, mobile telephones, PDAs, pagers, routers, switches, and the like. Embodiments may be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices. Program modules for one entity can be located and/or run in another entities data center or "in the cloud." In this specification and in the following claims, a computer system is also defined to include imaging systems (e.g., imaging system 102 in FIG. 1).

FIG. 1 illustrates an exemplary system 100 incorporating features disclosed or envisioned herein. At the heart of the system is a quantitative high-content cell imaging system 102 in which biological cells are scanned and analyzed. The exemplary cell imaging system 102 includes, but is not limited to, an imaging device 104 and a computing device 106.

Imaging device 104 comprises a stage housing 108 mounted on a microscope assembly 110. Stage housing 108 is configured to house the components required to position a specimen plate (such as, e.g., a 96-well plate) or a slide containing cells so microscope assembly 110 can image the cells to allow high content screening of the cells to be performed, as is known by one skilled in the art. Analyzing and storing of the data obtained from the imaging can be performed by imaging device 104 in conjunction with computing device 106.

Computing device 106 can be used as a controller for the system as well as for performing, by itself or in conjunction with imaging device 104, the analysis and/or storage of data obtained by imaging device 104. Computing device 106 can comprise a general purpose or specialized computer or server or the like, as defined above, or any other computerized device. Computing device 106 can communicate with imaging device 104 directly or through a network, as is known in the art. In some embodiments, computing device 106 is incorporated into imaging device 104.

System 100 can also include a user display device 112 to display results and/or system configurations. Imaging device 104 and/or computing device 106 can communicate, either directly or indirectly, with user display device 112.

The optical configurations generally arranged in imaging device 104 produce an enlarged image of cell(s) on a camera in order to record a high resolution image of the cell samples. In particular, the configurations discussed herein provide for a system that not only enables "wide-field" microscopy, as known to those skilled in the art, but also enables optical sectioning capabilities. This can include, e.g., standard confocal microscopy of a focused point or line of illumination scanned over a range of cells. These capabilities can be coupled with imaging algorithms, such as, e.g., Nearest Neighbor Deblurring (to be discussed below), which aid in providing the desired images as recorded by the camera.

In one embodiment, one or more of the method steps described herein are performed as a software application. However, embodiments are not limited to this and method steps can also be performed in firmware, hardware or a combination of firmware, hardware and/or software. Furthermore, the steps of the methods can exist wholly or in part on imaging device 104, computing device 106, and/or other computing devices.

An operating environment for the devices of the system may comprise or utilize a processing system having one or more microprocessors and system memory. In accordance with the practices of persons skilled in the art of computer programming, embodiments are described below with reference to acts and symbolic representations of operations or instructions that are performed by the processing system, unless indicated otherwise. Such acts and operations or instructions are referred to as being "computer-executed," "CPU-executed," or "processor-executed."

Figure 2:
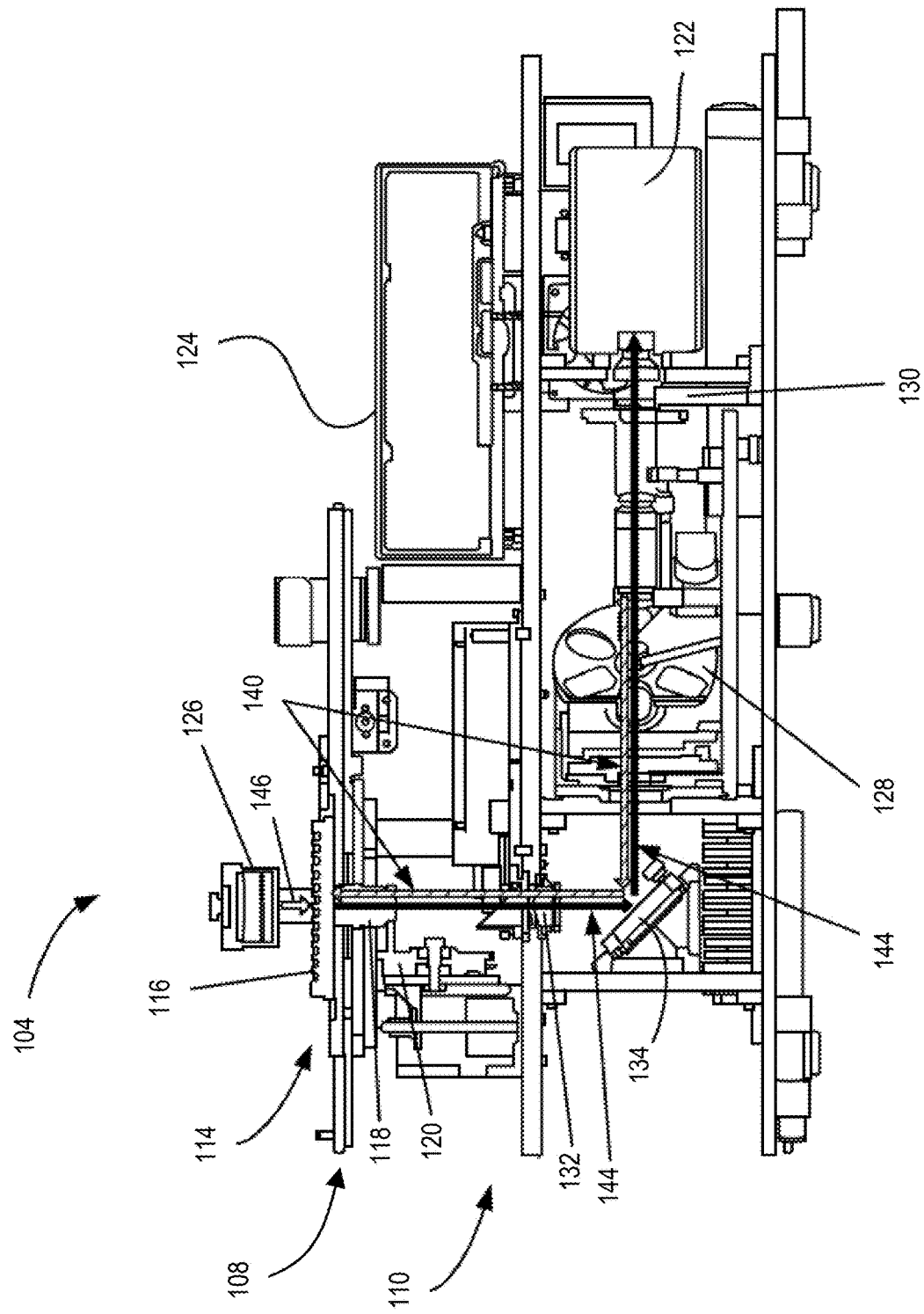
FIG. 2 is a cross sectional side view of a cell imaging device according to one embodiment.

FIG. 2 is an exemplary embodiment of imaging device 104. FIG. 2 displays a general cross-sectional side view of an interior platform design. In general, imaging device 104 integrates components required to position an HCS sample plate 116 containing biological cells so microscope assembly 110 can perform high content screening of the biological cells.

Stage housing 108 comprises a stage assembly 114 mounted in a manner so as to optically and mechanically cooperate with components that make up microscope assembly 110. Stage assembly 114 generally includes a stage on which HCS sample plate 116 can be positioned, as well as a stage positioning mechanism for selectively moving the stage for viewing, as is known in the art.

In the depicted embodiment, microscope assembly 110 houses an inverted microscope that can be used to perform screening of specimens on specimen sample plate 116 from underneath the specimens. The microscope includes an objective assembly 118 comprising a plurality of objectives, as is known in the art, to obtain magnified views of the specimens. Each objective can correspond to a different magnification level. In one embodiment at least three standard objectives are included. Additional objectives can also be included, if desired. Example standard objectives can include 10×/0.4 NA, 20×/0.45 NA and 40×/0.6 NA optical specifications. Example additional objectives can include 2×/0.08 NA, 4×/0.16 NA and 20×/0.7 NA optical specifications. Other magnification levels and objective types can also be used.

The microscope also includes a focus drive mechanism 120 mechanically coupled to microscope objective assembly 118. Objective assembly 118 can be moved up and down with respect to stage assembly 114 via focus drive mechanism 120 so as to align and focus any of the objectives of microscope objective assembly 118 on the biological cells disposed within specimen sample plate 116. Focus drive mechanism 120 can be an auto focus mechanism, although that is not required. Focus drive mechanism 120 can be configured with a stepper motor and screw/nut combination that reduces anti-backlash to provide a resolution of, e.g., down to 0.006-μm/microstep to support the microscope objectives configured in imaging device 104.

As an example embodiment to illustrate the objective workings of imaging device 104 when three objectives are utilized, objective assembly 118 can be configured in a custom made fashion to provide the three positions that enable interrogation of cells organized within sample plate 116. Focus drive mechanism 120 can rapidly and reliably switch between the objectives in an automated fashion. The objectives in such an arrangement are positioned often, but not necessarily, at 60-degrees apart, which can enable the primary objective to focus on sample plate 116 without the other two objectives interfering with the stage, sample plate 116 or other components within imaging device 104.

To change the objective, focus drive mechanism 120 can drop below stage assembly 114, rotate to the next objective position and then push the objective up to a proper focusing height. To provide enhanced system safety, a mechanical limit switch can be used to home the turret, while one or more optical TTL switches can be used to confirm that the position of the objective has been properly switched. In addition, each optical position can be held in place with an accurately machined mechanical detent on the rotating turret.

Although the discussion herein is geared toward the use of an inverted microscope configuration, it is to be appreciated that a non-inverted microscope configuration can alternatively be used to perform screening from above the cells. Moreover, although microscope assembly 110 discussed herein is custom made, other conventional microscope configurations can be incorporated when desired, such as for example, an Axiovert 200M manufactured by Carl Zeiss MicroImaging, Inc. in Goettingin, Germany. In some embodiments, a microscope is not required at all, as discussed in more detail below.

Microscope assembly 104 also comprises various known components used to generate and record images of the specimens obtained through the objectives. These components can include, but are not limited to:

- an image recorder 122 such as, e.g., a monochrome CCD or CMOS camera,
- a fluorophore excitation source 124 such as, e.g., light engine comprising multiple light emitting diodes (LEDs),
- optical filters that filter the excitation and emission lights, such as, e.g., a multi-position dichroic filter wheel 128 and a multi-position emission filter wheel 130, and
- light directing devices that direct the excitation and emission lights through the microscope assembly, such as, e.g., a telan lens 132, a fold mirror 134 (e.g., a 90-degree fold mirror), and one or more light tubes.

One or more of the above components are typically controlled by the computing device 106 to allow for automated imaging. The optical configuration generally arranged in imaging device 104 can produce an enlarged image of cell(s) on image recorder 122 so that a high resolution image of the cell samples can be recorded. In particular, the configurations discussed herein provide for a system that not only enables "wide-field" microscopy, as known to those skilled in the art, but also enables optical sectioning capabilities.

In one embodiment, telan lens 132 is a Near-Infrared (NIR) enhanced lens (e.g., an Olympus Triplet) designed for enhanced performance of imaging device 104 over the full range of the visible spectrum from blue to NIR when using any of the configured objectives with desired emission wavelengths, to be discussed below.

For fluorescent analysis, fluorophore excitation source 124 produces an excitation light that illuminates the cells and causes the cells to induce a fluorophore emission light. For example, fluorophore excitation source 124 can be a multi-LED light engine that works cooperatively with configured excitation filters provided by dichroic filter wheel 128 and emission filter wheel 130, both of which can be computer driven to select a desired filter.

As a general method of operation, fluorophore excitation source 124 can be automatically or manually directed to provide multiple bandwidths of light ranging from violet (e.g., 380 nm) to near infrared (e.g., at least 700 nm) and are designed to excite fluorophores, such as, e.g., cyan fluorescent protein (CFP) and Far Red (i.e., near-IR) fluorophores. Example LED bandwidths with appropriate excitation filters (e.g., as selected via computer 106 driven excitation filter wheel 130) can include, but are not limited to, Violet (380-410 nm LED & 386/23 nm excitation filter), Blue (420-455 nm LED & 438/24 nm excitation filter), Cyan (460-490 nm LED & 485/20 nm excitation filter), Green (535-600 nm LED & 549/15 nm excitation filter), Green (535-600 nm LED & 560/25 nm excitation filter), Red (620-750 nm LED & 650/13 nm excitation filter), and Near-IR (700-IR nm LED & 740/13 nm excitation filter). The two Green/excitation filter combinations listed above can be provided optionally via, for example, a mechanical flipper, when desiring to improve the brightness of red and scarlet dyes. Of course, other LED bandwidths can also be used.

Using system 100, fluorescent analysis of cells can be performed. To perform the analysis, stage assembly 114 first moves sample plate 116 to a position in which a desired particular segment of a micro-well or particular segment of a slide is in a given light path.

Figure 3:
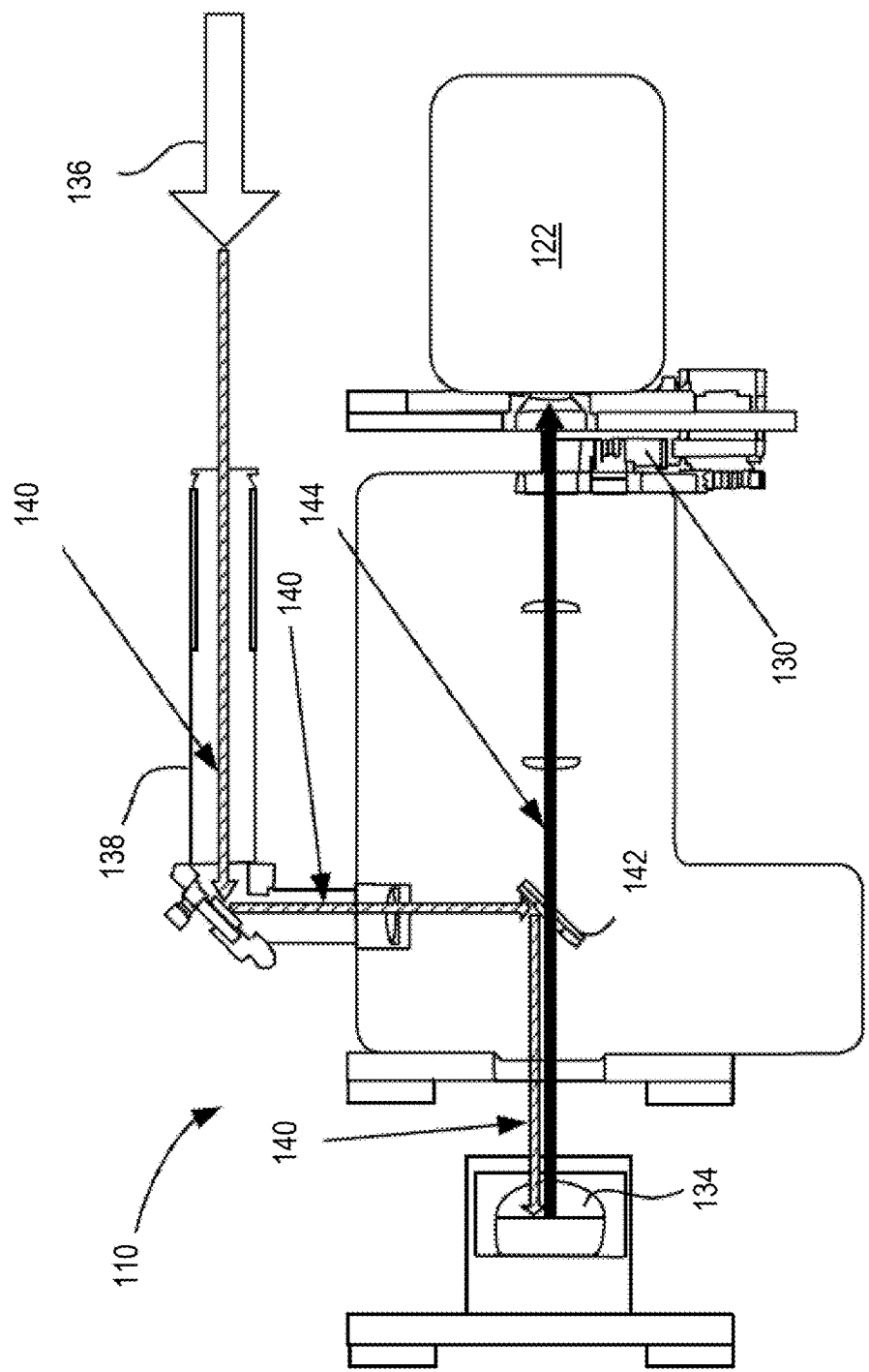
FIG. 3 is a cross sectional top view of the cell imaging device of FIG. 2, showing the flow of excitation and emission light through the device.

FIG. 3 is a top view depiction (as opposed to the side view of FIG. 2) that further illustrates the epifluorescent pathway of example components within microscope assembly 110. As depicted in FIGS. 2 and 3, fluorophore excitation source 124 emits a desired system wavelength bandwidth as relayed by a fiber optic delivery system, (as shown by large directional arrow 136 in FIG. 3), dependent on the application with respect to the fluorescently labeled cells in sample plate 116. The excitation wavelength bandwidth is guided by an illumination adaptor 138 using various optics so as to be further directed along an excitation light path 140 (as denoted in FIGS. 2 and 3 by the arrows containing slashes) until received by a desired dichroic component 142 (shown in FIG. 3) disposed in the multi-position dichroic filter wheel 128. Dichroic component 142 is designed and automatically software selected for the particular bandwidth of wavelengths provided by fluorophore excitation light source 124. Dichroic component 142 directs the excitation light to 90-degree fold mirror 134. Thereafter, as shown in FIG. 2, the excitation light continues upward along excitation light path 140 through telan lens 132 and objective assembly 118 to the cells disposed in sample plate holder 116, as known to those of ordinary skill in the art.

The excitation light induces a fluorescence in the cells disposed in sample plate holder 116. The induced fluorescence is returned from the cells via the epifluorescent arrangement back along a path 144 (shown by the dark arrows in FIGS. 2 and 3) through objective assembly 118 and telan lens 132 until received by 90-degree fold mirror 134. As particularly shown in FIG. 3, fold mirror 134 directs the induced fluorescent light back to dichroic component 142, which allows the induced fluorescent light to continue back along path 144 through, e.g., additional optical components. The induced fluorescent light is then optically filtered by a configured filter arranged in emission filter wheel assembly 130 and the filtered induced fluorescent light is captured and recorded as an image via camera 122.

As shown in FIG. 2, to also enable brightfield and chromophore imaging, microscope assembly 104 further comprises a transmission light assembly 126 positioned above sample plate 116. To perform chromophore analysis, cells are illuminated using various wavelength bandwidths of light to determine differential absorption measurements of chromophores within the cells. Because of transmitted light assembly 126, the transmission mode capabilities disclosed herein with respect to cell imaging system 102 provide in a novel manner for differential imaging so as to visualize standard chromophores and histological stains in a multiplexed manner. The imaging and visualization of chromophores is achieved by illuminating samples in the transmitted light geometry shown in FIG. 2 with light sources, such as LEDs, provided by the transmitted light assembly 126 having different colored wavelengths, e.g., blue, green, amber, & red, and detecting, using image recorder 122, differential absorption of the light by the chromophores.

Transmission light assembly 126 can also provide transmitted white light for brightfield imaging. The white light is used to "back-light" the fluorescently imaged cells in the micro-wells or slide segments (e.g., as disposed in sample plate 116). Some conventional high-content systems have been able to perform fluorescent and brightfield imaging in the same device, but none has been able to also provide a chromophore analysis.

Due to the unique and novel design of system 100, chromophore analysis can now be performed with fluorescent and brightfield analyses in the same high-content system to provide a three-pronged approach to high-content cell analysis. That is, all three modes (fluorescent, brightfield and chromophore) can be multiplexed in system 100 during high-content cell analysis.

Figure 4:
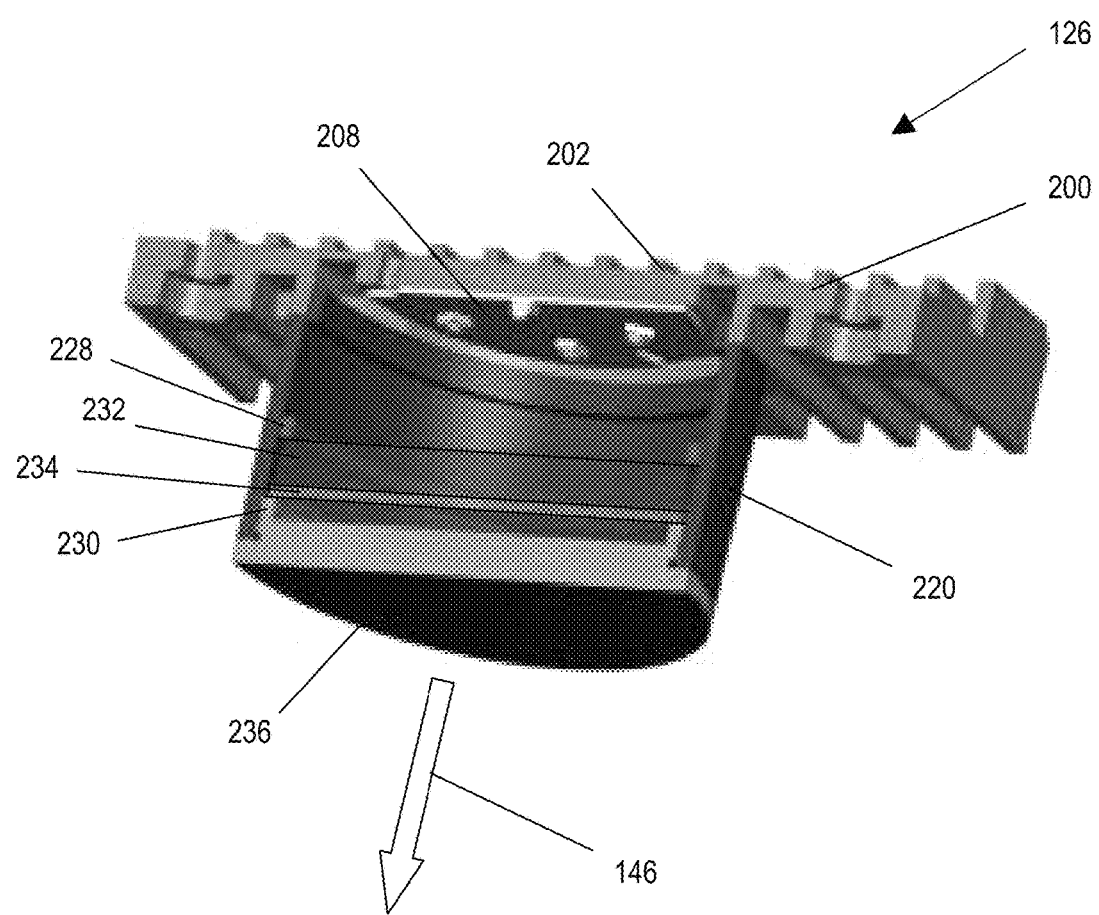
FIG. 4 is a cross sectional side view of a transmission light assembly according to one embodiment.
Figure 5:
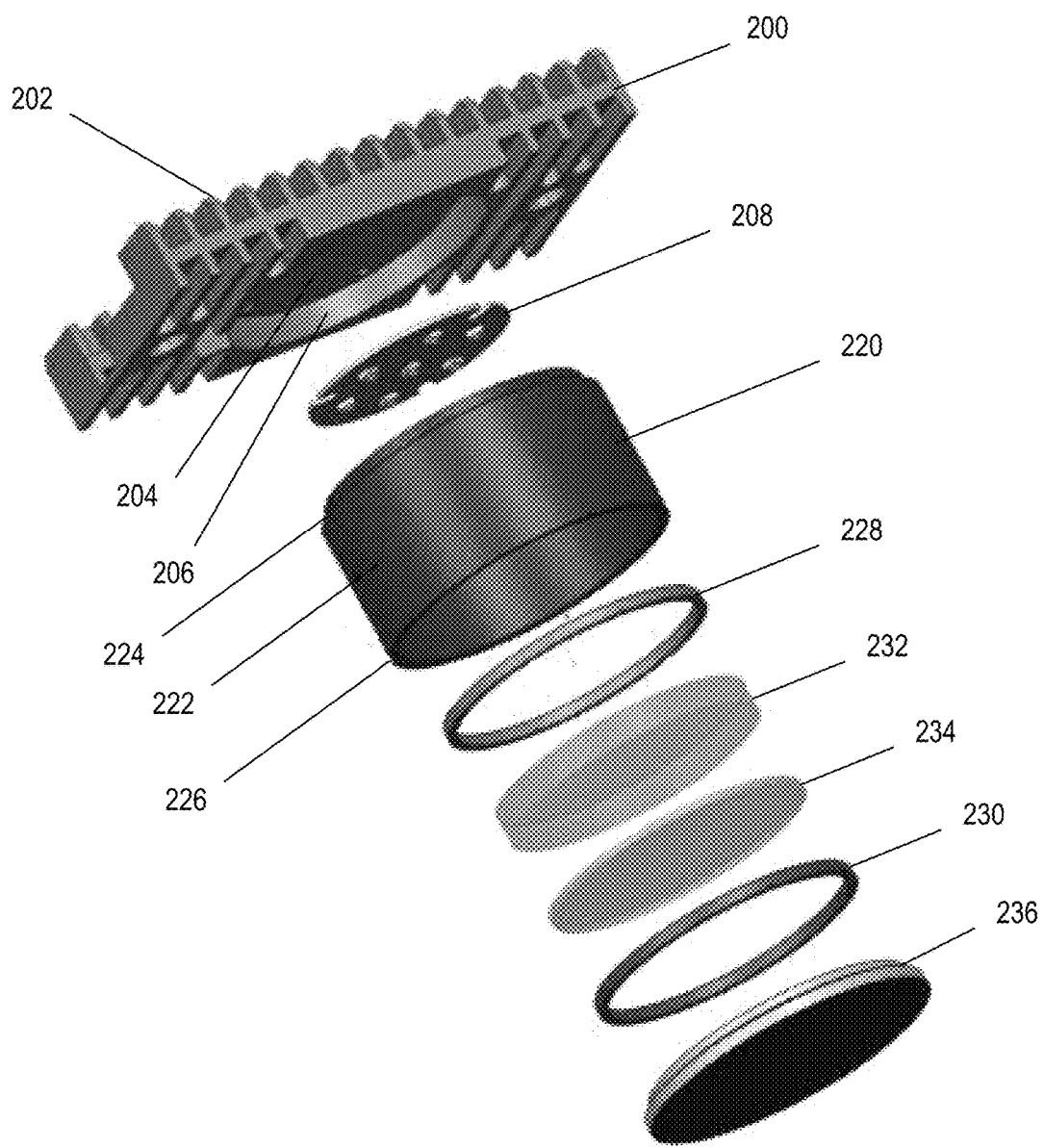
FIG. 5 is an exploded view of the transmission light assembly shown in FIG. 4.

FIGS. 4 and 5 depict cross-sectional and exploded views, respectively, of transmission light assembly 126. Transmission light assembly 126 can include a holder 200 having a plurality of fins 202 for cooling the assembly. If desired, transmission light assembly 126 can incorporate an active cooling mechanism, such as a fan or a liquid cooling system instead of or in addition to fins 202. Holder 200 can also include a recessed area 204 bounded by a circular sidewall 206. A light assembly 208 is secured within recessed area 204.

Figure 6:
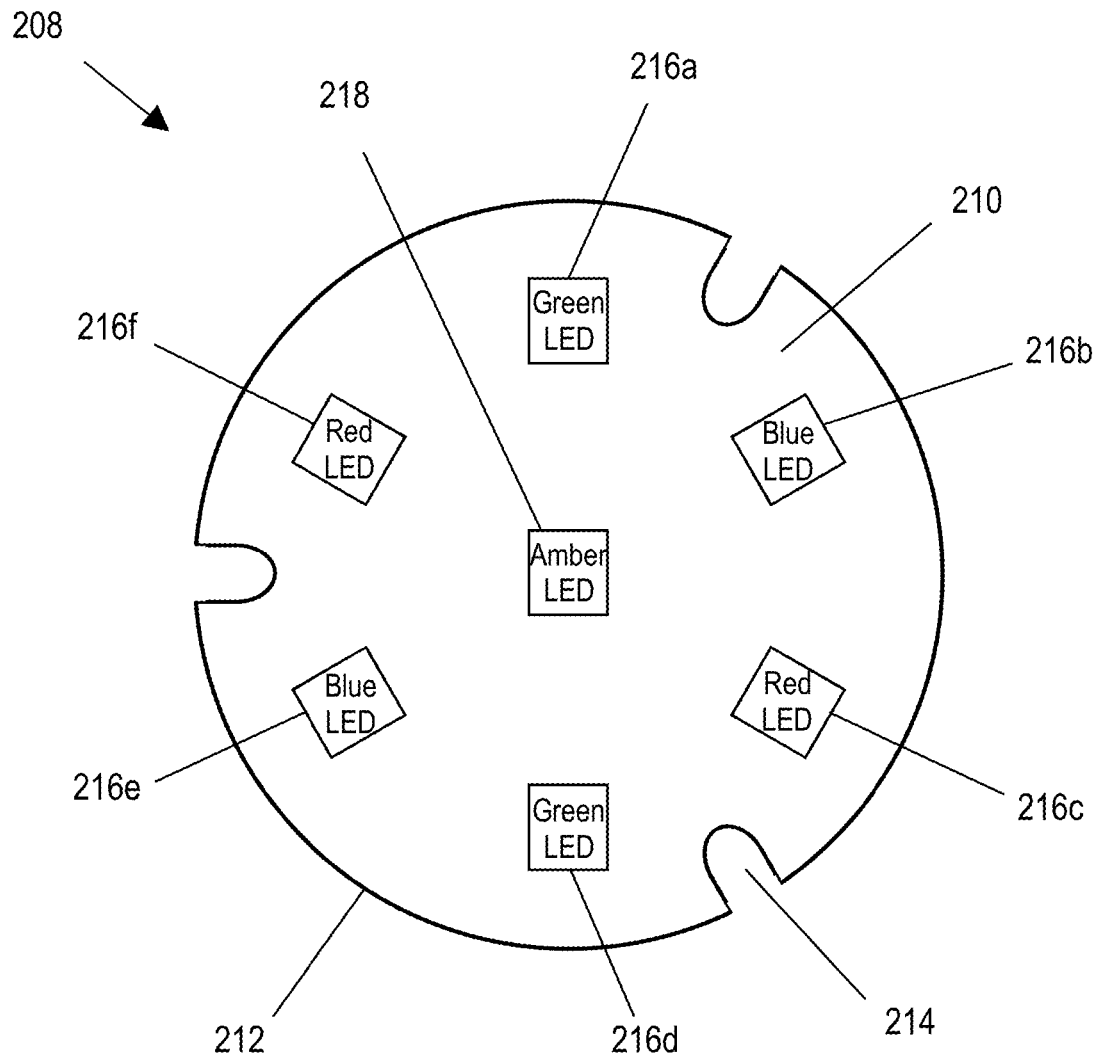
FIG. 6 is a top plan view of the light assembly shown in FIGS. 4 and 5.

Turning to FIG. 6, light assembly 208 comprises a main body 210 that is a flat, disc-like device having a perimeter edge 212. A plurality of notches 214 are positioned around perimeter edge 212 to help position light assembly 208 during installation on holder 200. Light assembly 208 further comprises a plurality of light sources, such as LEDs 216 (216a-216f), positioned in a particular pattern on main body 210 to allow transmission light assembly 126 to generate light for both brightfield and chromophore imaging.

As shown in FIG. 6, LEDs 216 are arranged in a generally circular pattern about main body 210. The encircling LEDs are spaced so that there is generally the same distance between adjacent LEDs, although this is not required. The LEDs are paired up in sets of two such that both LEDs of a light set emit the same color or wavelength when energized. For example, FIG. 6 depicts three different light sets—LEDs 216a and 216d form a first light set, LEDs 216b and 216e form a second light set, and LEDs 216c and 216f form a third light set. In the depicted embodiment, each light set is designed to emit one of three distinct wavelengths or colors—red, green, or blue. In addition, the LEDs in each light set are arranged on opposite sides of the circle from each other. In one embodiment, the LEDs in each light set are diametrically opposed to each other about a common center point.

Whenever any one of the colors or wavelengths is desired to be generated, both LEDs in a corresponding light set can be energized to emit the colored light from opposite sides of the circle. As a result, the light overlaps at the center point between the LEDs to provide a good mixing of the particular color. Furthermore, because the light sets all have the same center point, light emitted from two or more light sets at the same time results in a transmitted light that has a generally better color mixture in the middle of the transmitted light beam. Passing the colored light beam through a light diffuser further helps to color balance the light and obtain an even light distribution, as discussed in more detail below. As such, a balanced red, green, or blue light, alone or in any combination, can be generated by transmission light assembly 126 and shined downward onto sample plate 116 along transmission light path 146. Because different colors of light are used for different chromophores, this makes chromophore analysis possible.

Other light sources can be also used in combination with LEDs 216, if desired. For example, in the depicted embodiment, an optional LED 218 is also positioned on main body 210. LED 218 is positioned generally in the center of main body 210, but this is not required. LED 218 is designed to emit amber light when energized so as to be able to image and analyze chromophores that absorb the wavelength of light that corresponds to amber light, such as, e.g., taladium blue. LEDs that emit other colors can also be used.

Besides the ability to perform chromophore analysis, the above layout can also allow brightfield analysis to be performed. In particular, when the red, green, and blue light sets are energized at the same time, a white light is generated, which can be used for brightfield analysis. The LED layout, along with the light diffuser discussed below, result in a white light that has a good color balance and even light distribution across the light beam. As such, transmission light assembly 126 can generate the light required for both brightfield and chromophore analyses.

Example LEDs (Luxeon) that can be used in transmission light assembly 126 include: Amber (590 nm)-77 lm (LXML-PL01-0040), Green (530 nm)-125 lm (LXML-PM01-0070), Red-Orange (617 nm)-90 lm (LXML-PH01-0050), Royal-Blue (447.5 nm)-890 mW (LXML-PR02-0800), Green (530 nm)-125 lm (LXML-PM01-0070), Red-Orange (617 nm)-90 lm (LXML-PH01-0050), Royal-Blue (447.5 nm)-890 mW (LXML-PR02-0800).

LEDs are only one light source that can be used in transmission light assembly 126. Other wavelength sources can alternatively be used as light sources in place of the LEDs to generate the desired wavelengths, if desired.

Figures 7A, 7B, 7C:
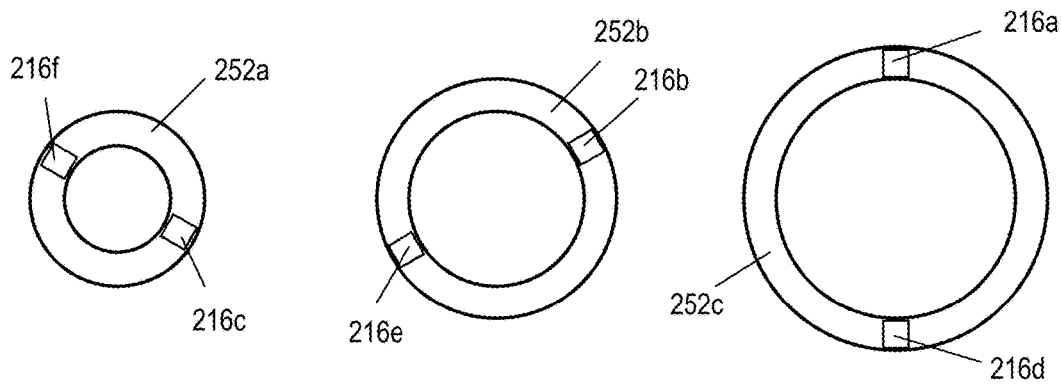
FIGS. 7A-7D are top plan views depicting an alternative embodiment of a light assembly.

FIGS. 7A-7D show an alternative embodiment of a light assembly 250. Similar to light assembly 208, light assembly 250 includes a plurality of LEDs 216 paired up in light sets so that the light sources in each light set are positioned on opposite sides of the circle from each other. However, instead of mounting all of the LEDs on a single main body, each of the light sets is mounted on a separate annular body or ring 252 (252a-252c). Thus, as shown in FIGS. 7A through 7C, the red, blue, and green colored LEDs are respectively mounted on rings 252a, 252b, and 252c. Of course, any ring can have any colored light set mounted thereto.

Rings 252 are sized so that they can fit together, one inside the other, about an optical center point 254, as shown in FIG.

Figure 7D:
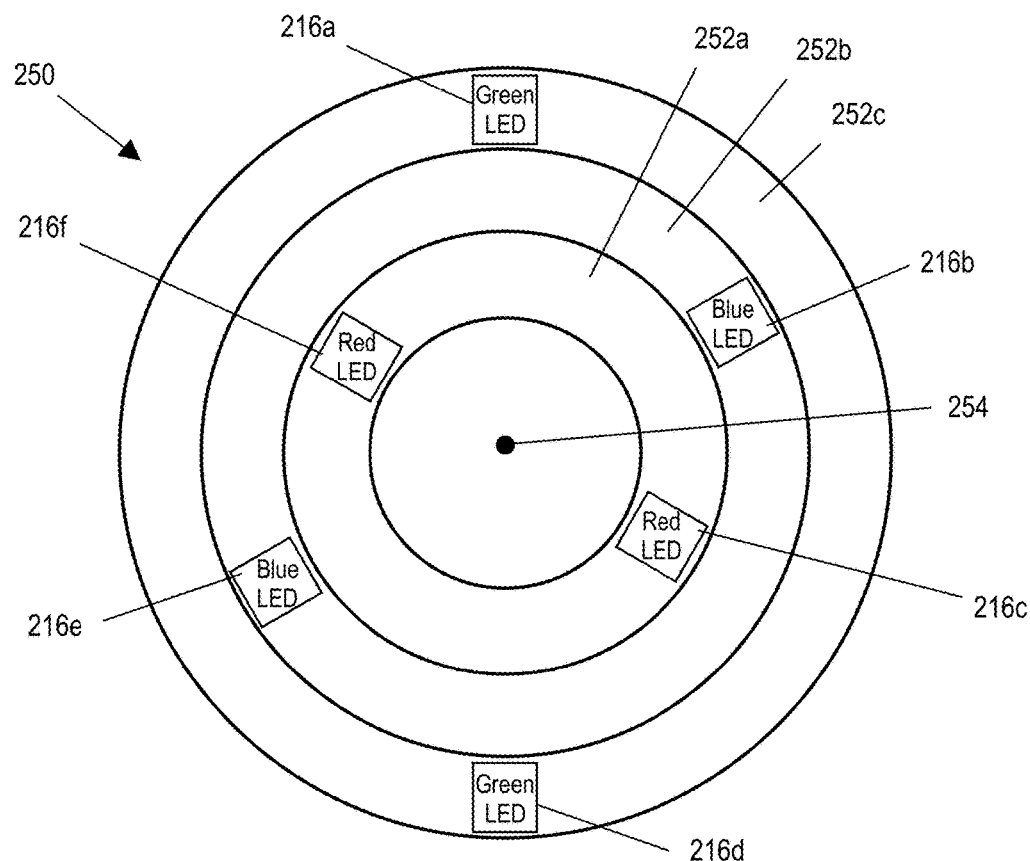

7D. As a result, each ring 252 can be rotated around center point 254 independent of the other rings to change the position of the LEDs mounted on that ring. As shown in FIG. 7D, the different light sets (i.e., LEDs of the same color) are positioned different distances away from the optical center point 254. However, for each light set, the LEDs of that light set are positioned on opposite sides of optical center point 254 the same distance. As a result, each ring 252 can be rotated about optical center point 254 as desired and the LEDs of that light set will remain on opposite sides of the optical center the same distance.

The use of separate rings 252 for each light set can be beneficial if the user desires to use different colored light sets for different applications. In that case, rings corresponding to the different light sets can be kept on hand in all of the ring sizes. The rings can then be mixed and matched as desired. That way, only rings corresponding to the desired wavelength(s) need to be swapped in for each application instead of replacing the entire light assembly.

Returning to FIGS. 4 and 5, transmission light assembly 126 also includes a lens tube 220 having an encircling sidewall 222 extending between a first end 224 and a second end 226. The first end 224 of encircling sidewall 222 is secured to circular sidewall 206 of recessed area 204 so as to encircle light assembly 208. In one embodiment, lens tube has a two-inch diameter. Other diameters are also possible. A first retaining ring 228 and a second retaining ring 230 are secured within lens tube 220 at the second end 226, with a light diffuser 232 and an anti-reflective (AR) window 234 being positioned within lens tube 220 between the retaining rings. An end cap 236 is removably secured to the second end 226 of the lens tube to protect the components of transmission light assembly 126 when not in use.

Light diffuser 232 is a mixing element that mixes together and homogenizes light as the light passes through the element. This alleviates problems that can arise when using different light sources, such as shading and uneven light distribution. Light diffusers can be made of any translucent object, such as, e.g., ground glass, greyed glass, Teflon, opalized glass or the like. The type of light diffuser to use can depend on the amount of loss vs. even distribution of light tradeoff that is desired. For example, ground glass diffusers can provide low scatter loss, holographic diffusers can increase transmission efficiency from a variety of light sources, UV holographic diffusers can provide increased performance in the ultraviolet range, and opal diffusing glass can generate a nearly Lambertian distribution of light, but cause higher levels of scattering loss. A frosted diffuser can also be used. In one embodiment, light diffuser 232 is an opalized light diffuser so that intensity is even from almost all angles. This even intensity, combined with the uniformity of LED placement, allows uniform illumination. One example of an opalized light diffuser that can be used is Opal Diffusing Glass Diffuser No. 46-106, manufactured by Edmund Optics.

AR window 234 further helps to provide an even light distribution by reducing reflection. It allows light to pass through in one direction but not in the other to reduce reflection of high-intensity light. The reduction in reflections improves contrast in an imaging system by elimination of stray light. AR window 234 is arranged in lens tube 220 so that light emitted from light assembly 208 can pass therethrough, but light from the other direction cannot. As such, AR window 234 prevents fluorescent light emissions that occur during fluorescent imaging from passing up through lens tube 220 and into LEDs 216, 218 which could cause an autofluorescing of the LEDs. Autofluorescing of the LEDs could cause a secondary excitation light to be transmitted down into the fluorophores, which could skew the fluorescent analysis.

In one embodiment, AR window 234 includes a coating designed to reflect light at the wavelengths associated with the light sources of light assembly 208, such as, e.g., 450-650 nm for LEDs 216 and 218. The coating is positioned on the surface of AR window 234 so that light transmitted by LEDs 216 and 218 at those wavelengths can pass through the coating, but light at those wavelengths that contacts the coating from the other direction is reflected, essentially blocking the light from passing through the coating. One example of an AR window that can be used is AR Coated Plastic Window No. 46-106, manufactured by Edmund Optics.

To provide the desired transmission light for performing brightfield and chromophore imaging, the appropriate light sets of LEDs 216 and/or LED 218 are energized. Each energized LED emits the wavelength of light corresponding to the LED color. The light from the energized LEDs is directed through lens tube 220 so as to pass through light diffuser 232 and AR window 234. The light exits lens tube 220 along transmission light path 146 as transmission light. Due to the layout of light assembly 208, as well as the light diffuser, the transmission light that exits transmission light assembly 126 via lens tube 220 has a good color balance between the colors emitted by the LEDs and has an even light distribution across the light beam, as discussed above.

Transmission light assembly 126 is positioned above sample plate 116 such that illumination light generated by transmission light assembly 126 is shined downward onto sample plate 116. If desired, transmission light assembly 126 can be configured on a boom arm (not shown) above sample plate 116 so that transmission light assembly 126 can swing out of the way when users access the sample plate or objectives.

For brightfield analysis all of the LEDs 216 can be energized to provide a white light to "back-light" the fluorescently imaged micro-wells or slide segments (e.g., as disposed in sample plate 116). For chromophore analysis, appropriate LEDs 216 and/or 218 can be energized to provide desired wavelength bandwidths of light to perform differential absorption measurements of chromophores. That is, when only one or two of LEDs 216 are energized (especially if the light source below the sample plate 116 is not), the differential absorption signature of the sample in the field can be selectively measured at a particular wavelength or combination of wavelengths.

During use, transmission light path 146 is aligned with epifluorescent return pathway 144 discussed above so as to provide illumination light to the fluorescently imaged micro-wells or slide segments (e.g., as disposed in sample plate 116). As the transmission light is shined onto the cells, the light is at least partially absorbed by the chromophores within the cells. The light that passes through the cells (i.e., the light that is not absorbed by the chromophores) is used to determine information about the chromophores and is defined herein as a chromophore absorption signature. Because of the alignment of transmission light path 146 with epifluorescent return pathway 144, the chromophore absorption signature follows along the same epifluorescent return pathway 144 so as to be eventually imaged by camera 122.

Because the pathway includes again passing through the dichroic filter wheel 128 and the multi-position emission filter wheel 130, the four transmitted light wavelengths that correspond to the respective individual LEDs 216 and 218 can be particularly selected so that they transmit through the multi-band dichroic mirror, e.g., a 5-band dichroic mirror disposed within the dichroic filter wheel 128, in addition to the multi-band emission filter, e.g., a 5-band component within multi-position emission filter wheel 130. Similarly, specific dichroic and emission filters can be selected to correspond with the wavelengths of the transmitted light For example, for the light emitted by an LED to be able to be captured by image recorder 122, the wavelength of the emitted light should be able to pass through at least one of the various filters in the light's path. To do that, the wavelength of the LED should lie within the transmission bandpass wavelength of at least one of the filters; otherwise the LED light will simply be filtered out and not reach image recorder 122. Therefore, care should be taken in selecting the LED wavelengths to be used in transmission light assembly 126.

Figure 8:
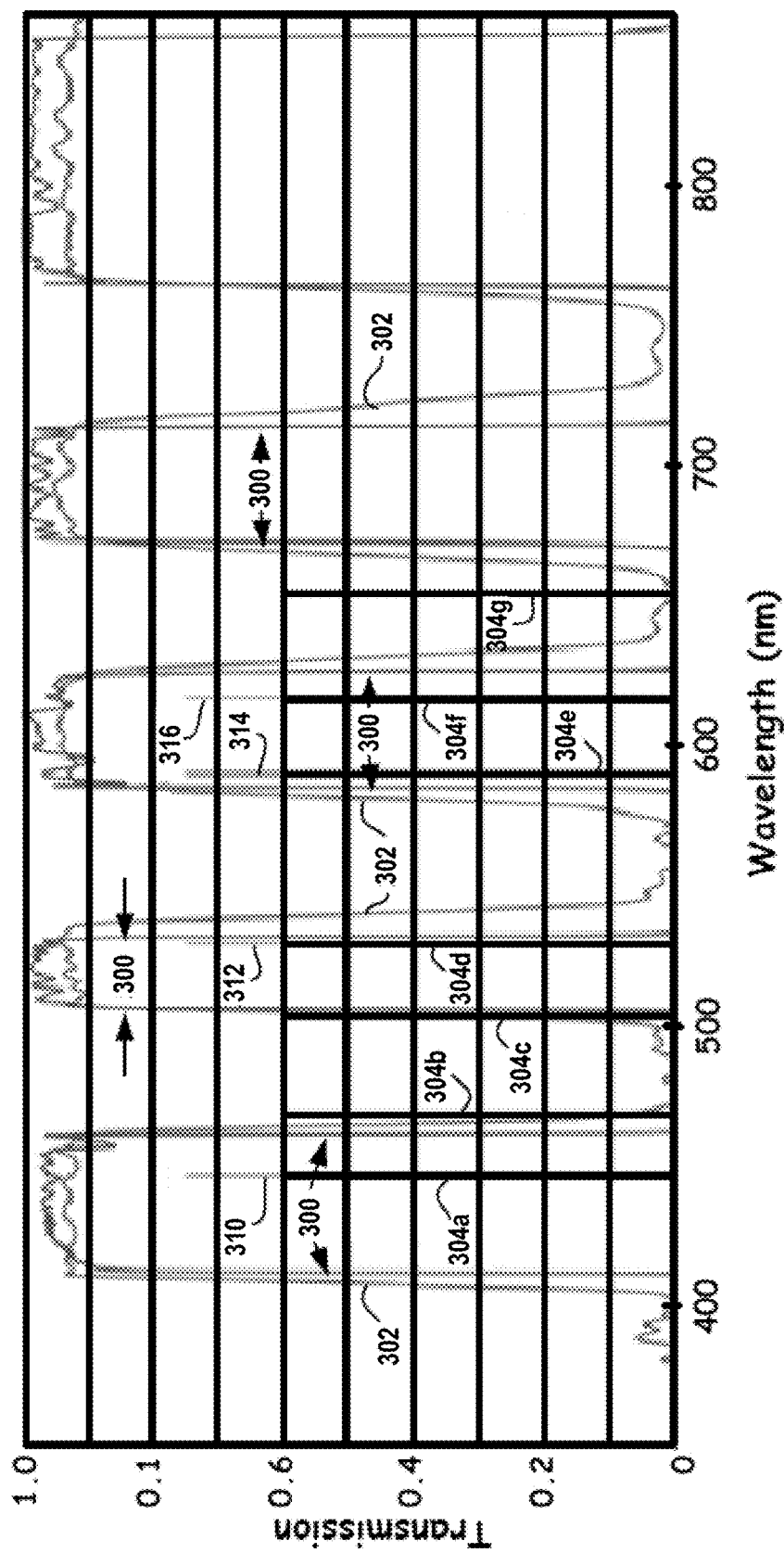
FIG. 8 shows a transmission versus wavelength plot for the dichroic mirrors and emission filters to be utilized with respect to selected transmitted light LEDs according to one embodiment.

FIG. 8 illustrates a means for selecting particular transmission LEDs to be utilized in one embodiment. FIG. 8, in particular, shows the transmission bandwidth characteristics versus wavelength for selected dichroics and emission filters according to one embodiment, plotted in combination with the emission wavelengths for various potential transmission LEDs. Reference character 300 denotes the emitter filter band-pass characteristics, reference character 302 denotes the dichroic mirror transmission band-pass characteristics, and reference characters 304 (304a-304g) denote transmission wavelengths for the various Luxeon LEDs listed above.

In the depicted graph, the transmission wavelengths 304a, 304d, 304e, and 304f are within the transmission bandpass wavelengths corresponding to both the emitter filter and the dichroic mirror, while transmission wavelengths 304b, 304c, and 304g are not. As such, only the LEDs corresponding to wavelengths 304a, 304d, 304e, and 304f should be considered for use in transmission light assembly 126 when the particular emitter filters and dichroics are used in imaging device 104. In light of this, reference characters 310 (Royal-Blue 447.5 nm), 312 (Green 530 nm), 314 (Amber 590 nm), and 316 (Red-Orange 617 nm), respectively corresponding to wavelengths 304a, 304d, 304e, and 304f, denote example compatible transmission light LED wavelength characteristics used in one embodiment.

FIGS. 9A-9E illustrate images captured on a CCD camera, used as image recorder 122, when using LEDs corresponding to the compatible transmission light LEDs discussed above to provide differential absorption images. Specifically, FIGS. 9A through 9D respectively show H&E stained tissue differential absorption images 320, 322, 324, and 326 captured with a 10× objective respectively using the four different wavelengths Blue 310, Green 312, Red 316, and Amber 314. FIG. 9E is a combined color image 328 (shown in black and white herein) of Red, Green and Blue that has been software assimilated by computing device 106 so as to provide details of the tissue not otherwise shown by the individual captured images.

As discussed above, embodiments can have several different microscope objectives with the ability to automatically switch between them. This can enable capabilities such as detecting a larger region with a low magnification objective, and then re-imaging particular areas of interest with higher magnifications.

Figures 10A, 10B:
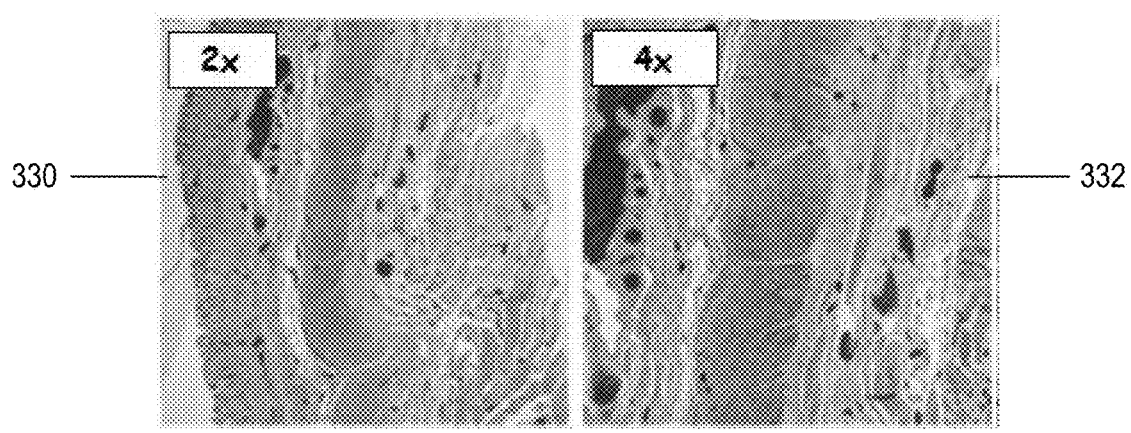
FIGS. 10A-10D illustrate different magnified images of a chromophore stained tissue using transmitted light capabilities according to one embodiment.
Figures 10C, 10D:
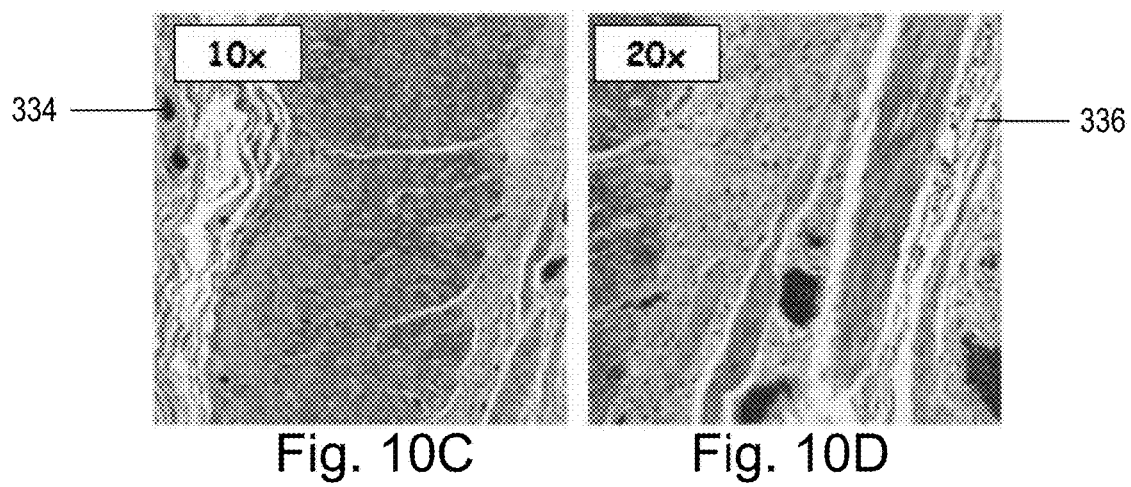

For example, FIG. 10 shows different magnified images of the same chromophore stained tissue using transmitted light. Specifically, FIG. 10a through 10d respectively show H&E stained tissue differential absorption images 330, 332, 334, and 336 using automated imaging capabilities at 2×, 4×, 10×, and 20× magnification levels.

Accordingly, in addition to fluorescently labeled samples, this capability can now be automatically applied to chromophore labeled samples, or samples containing a combination of different modes. In one embodiment, the switch to a higher magnification can be triggered by the automatic detection of particular objects or staining patterns of interest in a lower magnification image.

Thus, FIGS. 9 and 10 illustrate that in combining the ability to detect both fluorescence and chromophores, various embodiments maximize capability in both imaging modes.

For fluorescence, this means being able to excite fluorophores and detect their emitted fluorescence over the entire visible spectrum, ranging, e.g., from near-UV to near-IR.

For chromophores, this means being able to detect absorbance signatures caused by chromophore absorption over the range of the visible spectrum.

In one embodiment, to achieve this goal in fluorescence, fluorophore excitation source 124 comprises an LED light source that emits in 7 different wavelength bands, spanning the entire visible spectrum. Computer-controlled multi-position dichroic filter wheel 128 is used to contain dichroic mirrors and computer-controlled multi-position emission filter wheel 130 (e.g., 6-position filter wheel) is used to contain emission filters, independent of the dichroic filter wheel. Emission filter wheel 130 is positioned just before image detector 122, which is a low light-level CCD camera. The multi-position dichroic filter wheel 128 and emission filter wheel 130 both contain single band mirrors or filters which are dedicated to transmitting a specific wavelength band, or multiband mirrors or filters that can transmit multiple bands simultaneously. This can include a 5-band dichroic mirror and emission filter pair that can simultaneously transmit 5 or more wavelength bands. Furthermore, due to the independent computer-control and selection ability of the excitation LEDs, dichroic mirrors, and emission filters, non-conventional fluorescence imaging modes can also be used, such as Fluorescence Resonance Energy Transfer (FRET), ratiometric fluorescence imaging, or imaging with fluorescence probes with long Stokes shifts (such as Quantum Dots) (Byers et al., 2007).

FIG. 11 shows absorption bands of 35 common chromophores used for biological staining (as recreated from Olympus Microscopy resource Center) of cells. Overlaid on FIG. 11 are four wavelengths (denoted by element numbers 340, 342, 344, and 346) corresponding to four LEDs used in one embodiment of the transmitted light assembly. The wavelengths 340, 342, 344, and 346 respectively correspond to 448 nm (Royal-Blue), 530 nm (Green), 590 nm (Amber), and 617 nm (Red-Orange). As depicted in FIG. 11, the absorption band of each of the listed chromophores includes at least one of the wavelengths 340, 342, 344, and 346. Thus, at least one of the four LED wavelengths is differentially absorbed by each of the listed common chromophores over the visible spectra. As such, each of the listed chromophores can be utilized for differential absorption imaging of cells disposed within sample holder 116. This enables a wide range of chromophore options that can be used by imaging system 100.

In light of this, adding transmission light assembly 126 to an epifluorescent platform enables many different options for the imaging of fields. For example, cell imaging system 102 can allow for fluorescent-only measurement, absorption-only measurement or a combined fluorescent/absorption measurement in which the field of the sample is illuminated concurrently from the top and bottom. As an added benefit, the LED sources can also be operated as a white light emitter for brightfield analysis. As such, they are not only cost effective with respect to typical broadband sources but also provide for an overall module that is relatively small and very easy to add to an existing fluorescence microscope.

Because of the multi-optical imaging capability, multiple fields of multiple wells or micro-wells of a high-content plate can be automatically imaged in any of the imaging modes. For example, each field can be positioned within the epifluorescent 140 or transmitted light path 146 and imaged, as shown in FIG. 2. Such micro-wells can be imaged by imaging device 104 within given times, with the stage assembly 114 moving the sample plate 116 (e.g., a microwell plate or microscope slide) in small increments so that successively one field after another can be positioned in the light path 140 or 146 and imaged. For example, in a typical embodiment a field corresponds to 1/300th of the bottom surface of a micro-well and imaging can begin with four fields at the center of the micro-well, followed by the twelve fields surrounding the central four fields, followed by the forty-eight fields surrounding the twelve, etc. until the imaging device 104 using either the epifluorescent or transmitted light or combination has provided enough images to capture a defined number of "valid" cells.

Thus, using an HCI system such as the system shown in FIG. 1, high content imaging can be performed using chromophore imaging alone. For example, in one method of high-content cell analysis, a plate can be positioned on a stage assembly of an imaging system, the plate having a plurality of wells, each well having positioned therein biological cells with chromophore stained molecules. Then, for each well of the plurality of wells, the stage assembly can be moved so the well becomes aligned with an optical path, transmission light can be directed at the biological cells within the well to induce the biological cells to emit a chromophore absorption signature along the optical path, and an image of the induced chromophore absorption signature emitted from the biological cells within the well can be recorded. Finally, the chromophore absorption signature recorded for each well can be analyzed.

Alternatively, imaging can be performed that incorporates both fluorescent and chromophore imaging using a single apparatus. The imaging can be performed at separate times. For example, in one method of cell analysis, a container containing biological cells comprising fluorescent reporter molecules and chromophore stained molecules can be positioned so that the container becomes aligned with an optical path. The biological cells can be excited with excitation light to induce the biological cells to emit a fluorescent light along the optical path and an image of the induced fluorescent light can be recorded. A transmission light can be directed at the biological cells to induce the biological cells to emit a chromophore absorption signature along the optical path and an image of the induced chromophore absorption signature can also be recorded. Finally, the biological cells can be analyzed using data from the two recorded images.

Alternatively, the imaging can be performed concurrently. For example, in one method of cell analysis, a container containing biological cells comprising fluorescent reporter molecules and chromophore stained molecules can be positioned so that the container becomes aligned with an optical path. The biological cells can be excited with excitation light and a transmission light can be directed at the biological cells to induce the biological cells to concurrently emit a fluorescent light and a chromophore absorption signature along the optical path and an image of the concurrently induced fluorescent light and chromophore absorption signature can be recorded. Finally, the biological cells can be analyzed using data from the image.

In some embodiments "channels" can be used for imaging and analysis. That is, multiple images can be taken for each field, each corresponding to a different channel. A channel (i.e., optical modality) is typically defined by a particular excitation light (LED or filtered white light), a particular imaged light (usually filtered from what is received from the micro-well), a particular exposure period, etc. Each image can be retained, effectively, as a black-and-white signal, with information about the channel also being saved, such as the excitation signal, the exposure period, and the like. Other image information can also be saved. Thus, if, e.g., 100 fields are imaged, each using three different channels, 300 images can be retained and stored along with information regarding each channel. One or more of the recorded images can be used to analyze each field. For example, in the example above, each field can be analyzed using any number of the three different channels corresponding to the channels of the field.

To overcome the limitations of a single monochrome image recorder 122 (such as a monochrome CCD or CMOS camera) utilized in common HCI instruments, new multi-modality optical capabilities are introduced herein that are not provided by conventional HCI platforms. In particular, instead of using different detectors to each detect a separate primary wavelength, a single monochrome detector can be used to acquire multiple images, each corresponding to a separate wavelength. For example, transmission light assembly 126 can illuminate the sample with different distinct wavelengths at different times so that monochrome camera 122, used for fluorescence, can acquire images corresponding to each of the wavelengths, as discussed above with respect to FIGS. 9A-9D.

The result is a system arrangement and methodology that in a novel fashion, can use a single detector to capture multiple images distinguished by wavelength selection via a selected excitation band-pass filter or selected filter in operation with the array of multiple narrow-band sources (e.g., four LEDs) assembled in transmission light assembly 126. For example, in one method of cell analysis, a container containing biological cells having chromophore stained molecules can be positioned on a stage assembly of an imaging system so that the container becomes aligned with an optical path. Different wavelengths of transmission light can then be directed, one at a time, at the biological cells to induce the biological cells to emit different chromophore absorption signatures along the optical path. Each of the induced chromophore absorption signatures corresponding to the different transmission wavelengths can then be separately recorded. A composite image can then be generated by a computerized device based on the recorded images.

In one embodiment, a liquid crystal tunable filter (LCTF) can be used in place of emission filter wheel 130 to provide the wavelength selection. Such filters operate like a filter wheel with dozens or hundreds of filters but with the benefit of having no moving parts. Such tunable filters transmit narrow bands of light whose peak positions can be electronically tuned to virtually any wavelength at a high precision, e.g., to about 1 nanometer precision, and within short time frames, e.g., in the millisecond range. Such filters are incorporated herein as an alternative embodiment to provide a wide desired spectral range such, as for example, in the Visible (e.g., 420-720 nm).

In one embodiment, the imaging "channels" can be used to facilitate automatic imaging in which images are analyzed in real-time to determine if further images are needed and what portion of the field should be captured. Thus, while imaging is ongoing, cell imaging system 102 can compare images and generate data. While the imaging software can overlay images of one or more fields to achieve a multi-color image with high-contrast, such a mode of operation is usually not done for the field as a whole.

Instead, a first image (for example, using Hoechst stain to give the cell nucleus a fluorescent pattern at wavelength 1) can be acquired and used to define position, size, shape, etc. of each cell nucleus in the field. Mathematics can then be used to define expected areas of cell cytoplasm (around each nucleus), e.g., in an annular-type shape (so many pixels out from the cell nucleus). Each such annular shape can then be mathematically superimposed on the images of the same field in Channel 2 and Channel 3. Data can be derived from Channels 2 and 3 giving information regarding how much of a component stained by a fluorescent dye is active and ready to be excited and imaged in Channels 2 and 3, respectively, which is in the annular shape where each cell is inferred to be and/or in the nuclear region actually measured in channel 1. The system can be programmed to perform a variety of complex analyses of the images of the same field in multiple channels, both while the system is taking additional images of other fields and against stored images from prior runs.

It is in this context that the system herein can perform "automated" analyses, repeated for multiple fields in a well, multiple wells in a plate and multiple plates in an experiment. Once all of the parameters have been defined, the instrument can run and analyze essentially unattended.

For example, in one method of automated cell analysis, a container having an array of locations that contain a plurality of cells having one or more fluorescent reporter molecules and one or more chromophore stained molecules can be positioned on an imaging system. The plurality of cells in each of the locations can be contained as a subset plurality of cells to provide for a plurality of fields and the imaging system can have first and second light sources configured to selectively direct one or more wavelengths of radiation to the plurality of fields in any of the array of locations. The first light source can be configured to generate excitation light that induces the biological cells to emit a fluorescent signal and the second light source can be configured to generate transmission light that induces the biological cells to emit a chromophore absorption signature.

Each of the fields within one or more desired locations can be imaged by recording multiple images for each field with an image recorder. Each of the images can comprise a fluorescent signal induced by the first light source or a chromophore absorption signature induced by the second light source, on or within the cells and each image can comprise at least one optical modality selected from: one or more excitation wavelengths of radiation, a selected filtered wavelength of radiation, and a desired imaging exposure period.

Each of the recorded images can be compared so as to convert the induced fluorescent signals and chromophore absorption signatures from each of the multiple images into digital data;

The digital data can be utilized to automatically determine intensity and/or distribution of the induced fluorescent signals from the fluorescent reporter molecules on or within cells and automatically determine intensity and/or distribution of the induced chromophore absorption signatures on or within the cells. Changes can indicate a change in the distribution, environment or activity of the fluorescent reporter molecules or chromophore on or within the cells.

System 100 also includes software that runs the system. Such software can reside on computing device 106 to control all the necessary instrument hardware such as, but not limited to, stage assembly 114, objective assembly 118, focus drive mechanism 120, dichroic filter wheel 128, and emission filter wheel 130. The software can also selectively control the wavelengths to be provided by excitation light source 124 and transmission light assembly 126 and determine when to capture images on image recorder 122. Computing device 106 can also enable analysis of the captured images, display the results on monitor 112 and manage data that can also be provided in an integrated database.

Moreover, in analysis of the captured images using confocal microscopy, computing device 106 can implement any number of image processing algorithms to process captured image information as desired. As an example, such an algorithm can include optical sectioning coupled with Nearest Neighbor Deblurring, as briefly touched on above. Such a routine configured herein is often applied to cell fluorescent structures distributed discretely, especially in the z-axis. In particular, the inclusive computing device 106 algorithm, if desired by an operator, can apply an operation plane-by-plane to each two-dimensional plane of a three-dimensional image stack captured by image recorder 122. For example, the nearest-neighbor algorithm operates on the z-plane by blurring the neighboring planes (z+1 and z−1, using a digital blurring filter), then subtracting the blurred planes from the z-plane. This technique can also be user selectable to a number of neighboring planes. Moreover, a three-dimensional stack (i.e., optical sectioning) can also be processed by applying the algorithm to every plane in the stack. In such an algorithmic operation, an estimate of the blur can be removed from each plane.

As noted above, in some embodiments, the objectives or even the entire microscope can be omitted from the system. By way of example and not limitation, the transmission light assembly can also be used with:

Systems that incorporate microlens arrays instead of objectives,

Systems in which the cells are placed on a flatbed scanner and imaged using a closed-circuit television lens, and Systems in which the cells are placed directly on a detector.

These systems can incorporate detectors, such as CCD or CMOS sensor arrays or chips, that image larger areas at a high resolution. Because of this, the field-of-view (FOV) can be much larger than what can be obtained using standard objectives, meaning that the size of the imaged area of the biological cells can be larger. For example, in the large FOV systems the size of the imaged area can be several centimeters in length, opposed to about a millimeter in length using standard objectives.

As a result, the objectives and/or many of the other portions of the microscope assembly may be omitted. For example, in one embodiment the cells can be placed directly on an image recorder that incorporates the large FOV detectors, effectively eliminating the need for most, if not all, of the microscope assembly. Also a result, the biological container, such as the sample plate or slide, may not need to be moved as much to image all of the cells. For example, in one embodiment a plurality of wells may be imaged without moving the container. In some embodiments, all of the cells within the entire container may be imaged without moving the container.

Irrespective of the microscope setup (or omission), the system can still incorporate a transmission light assembly positioned to direct a transmission light to the biological cells to induce a chromophore absorption signature from the cells. Such a system can also incorporate a fluorophore excitation source that directs excitation light to the biological cells to induce a fluorophore emission light from the cells.

It is to be understood that features described with regard to the various embodiments herein may be mixed and matched in any desired combination. In addition, the concepts disclosed or envisioned herein may be embodied in other specific forms. The described embodiments are to be considered in all respects only as illustrative and not restrictive. The scope is, therefore, indicated by the appended claims rather than by the foregoing description. All changes which come within the meaning and range of equivalency of the claims are to be embraced within their scope.

What is claimed is:

1. An automated method of cell analysis using a high-content imaging system, the high-content imaging system having a fluorophore excitation source, a transmission light assembly, and a container with a plurality of wells, each well having positioned therein or thereon biological cells comprising chromophores and fluorescent reporter molecules, the method comprising:
for each well of the plurality of wells:
aligning the well with an optical path of the high-content imaging system;
directing transmission light from the transmission light assembly at the well to induce the biological cells within the well to emit chromophore absorption signatures along the optical path, wherein the transmission light emits a plurality of wavelengths, such that each wavelength induces a different chromophore absorption signature;
directing excitation light from the fluorophore excitation source of the high-content imaging system at the well to induce the biological cells to emit induced fluorescent light from the fluorescent reporter molecules along the optical path;
imaging, by a same imaging device of the high-content imaging system, an image of each induced chromophore absorption signature;
imaging an image of the induced fluorescent light; and
automatedly and sequentially or concurrently imaging the chromophore absorption signature and the fluorophore emission light;
recording the imaged chromophore absorption signature and the fluorophore emission light as one or more images; and
generating, by a computerized device, a composite image of the biological cells of the well based on the images of the induced chromophore absorption signatures and the induced fluorescent light imaged by the imaging device.

2. The method recited in claim 1, wherein the transmission light assembly emits each of the plurality of wavelengths at separate times from each other.

3. The method recited in claim 1, wherein the imaging device of the high-content imaging system is a monochrome imaging device.

4. The method recited in claim 1, further comprising analyzing, by the computerized device, the imaged chromophore absorption signatures to determine intensity and distribution of the induced chromophore absorption signatures.

5. The method recited in claim 1, wherein for each well, the steps of directing the transmission light at the well and directing the excitation light at the well are performed concurrently.

6. The method recited claim 1, wherein for each well, imaging the image of the induced fluorescent light is performed by the same imaging device used to image the induced chromophore absorption signatures.

7. The method recited claim 1, further comprising analyzing, by the computerized device, the imaged chromophore absorption signatures and the imaged fluorescent light of the biological cells to determine changes in the distribution, environment, and activity of the fluorescent reporter molecules and chromophores on or within the cells.

8. An automated method of cell analysis using a high-content imaging system, the high-content imaging system having a fluorophore excitation source, a transmission light assembly, and a container with a plurality of wells containing biological cells that have been labeled with one or more fluorophores and one or more chromophores, the method comprising:
for each well of the plurality of wells:
directing transmission light from the transmission light assembly at the well to induce a chromophore absorption signature along an optical path of the high content imaging system from the one or more chromophores labeling the biological cells;
directing excitation light from the fluorophore excitation source at the well to induce fluorophore emission light along the optical path from the one or more fluorophores labeling the biological cells;
automatedly and sequentially or concurrently imaging the chromophore absorption signature and the fluorophore emission light; and
recording the imaged chromophore absorption signature and the fluorophore emission light as one or more images.

9. The method recited in claim 8, further comprising, for each well of the plurality of wells, generating a composite image of the biological cells of the well based on the imaged chromophore absorption signature and the imaged fluorophore emission light.

10. The method recited in claim 8, wherein the transmission light emits a plurality of wavelengths, such that each wavelength induces a different chromophore absorption signature.

11. The method recited in claim 10, further comprising, for each well of the plurality of wells:
selectively producing the plurality of wavelengths such that each wavelength of the plurality of wavelengths is directed to the well at separate times to induce a plurality of chromophore absorption signatures from the one or more chromophores labeling the biological cells;
imaging and recording each of the plurality of chromophore absorption signatures; and
generating another composite image of the biological cells based at least on the plurality of imaged chromophore absorption signatures.

12. The method recited in claim 10, wherein selectively producing the plurality of wavelengths comprises selectively energizing a plurality of light sources arranged about the optical axis.

13. The method recited in claim 8, wherein directing transmission light from the transmission light assembly at the well comprises selectively energizing a plurality of light sets, each light set having a pair of light sources positioned on opposite sides of an optical axis.

14. The method recited in claim 13, wherein selectively energizing the plurality of light sources additionally comprises selectively energizing at least one light source positioned generally at a center of the optical axis.

15. The method recited in claim 13, wherein each light set is selectively energizeable with respect to each other light set of the plurality of light sets.

16. The method recited in claim 15, wherein each first light source in the pair of light sources is selectively energized at a same energized state as each second light source in the pair of light sources.

17. The method recited in claim 13, wherein selectively energizing the plurality of light sources comprises selectively energizing one or more light sources of the plurality of light sources having a same wavelength of light.

18. The method recited in claim 13, wherein selectively energizing the plurality of light sets comprises selectively energizing one or more of:
   a first light set comprising 617 nm red lights;
   a second light set comprising 530 nm green lights; and
   a third light set comprising 447.5 nm blue lights.

19. The method recited in claim 18, wherein energizing the first, the second, and the third light sets produces a white light, the white light having an even light distribution, wherein the white light allows a bright field analysis of the well.

20. The method recited in claim 19, further comprising multiplexing the bright field analysis with the fluorophore emission light and the chromophore absorption signature.

* * * * *